United States Patent
Vos et al.

(10) Patent No.: US 11,647,800 B2
(45) Date of Patent: May 16, 2023

(54) VIBROTACTILE FEEDBACK ARRANGEMENT

(71) Applicant: ELITAC B.V., Utrecht (NL)

(72) Inventors: Wouter Karel Vos, Utrecht (NL); Tine Joke Spikker-Titsing, Utrecht (NL)

(73) Assignee: ELITAC B.V., Utrecht (NL)

( * ) Notice: Subject to any disclaimer, the term of this patent is extended or adjusted under 35 U.S.C. 154(b) by 0 days.

(21) Appl. No.: 17/631,133

(22) PCT Filed: Jul. 28, 2020

(86) PCT No.: PCT/NL2020/050489
§ 371 (c)(1),
(2) Date: Jan. 28, 2022

(87) PCT Pub. No.: WO2021/020967
PCT Pub. Date: Feb. 4, 2021

(65) Prior Publication Data
US 2022/0264972 A1   Aug. 25, 2022

(30) Foreign Application Priority Data

Jul. 29, 2019 (NL) .................................. 2023588

(51) Int. Cl.
*A41D 13/12* (2006.01)
*A41D 1/00* (2018.01)
(Continued)

(52) U.S. Cl.
CPC ......... *A41D 13/1281* (2013.01); *A41D 1/002* (2013.01); *A63B 26/003* (2013.01);
(Continued)

(58) Field of Classification Search
CPC .. A41D 13/1281; A41D 1/002; A63B 26/003; A63B 71/0619; A63B 2071/0655;
(Continued)

(56) References Cited

U.S. PATENT DOCUMENTS

| 9,282,897 B2 * | 3/2016 | Ross, Jr | A61B 5/0022 |
| 2015/0018724 A1 * | 1/2015 | Hsu | A61B 5/4023 |
| | | | 600/595 |
| 2017/0135612 A1 | 5/2017 | Singhatat | |

FOREIGN PATENT DOCUMENTS

WO        2009029834 A1     3/2009

OTHER PUBLICATIONS

International Preliminary Report on Patentability; Chapter II; PCT Patent Application No. PCT/NL2020/050489; dated Nov. 4, 2021; 7 pages.

(Continued)

*Primary Examiner* — Sundhara M Ganesan
(74) *Attorney, Agent, or Firm* — AEON Law, PLLC; Adam L. K. Philipp; David V. H. Cohen

(57) ABSTRACT

Bilateral vestibular loss is a chronic condition of which the causes can be ototoxic, infectious, traumatic, autoimmune or congenital. An object of the invention is to improve the effectiveness of a vibrotactile feedback arrangement. The current invention provides a vibrotactile feedback arrangement for use arranged to a human body, comprising: a sensor arranged for sensing a current attitude of the human body relative to the environment; tactile actuators arranged for allowing the human body to perceive an attitude deviation; an elongated carrier for holding the tactile actuators and the sensor in tactile communication with the human body and for holding the tactile actuators and the sensor substantially fixed relative to the human body; and a processing unit configured for: receiving the current attitude from the sensor; determining the attitude deviation based on comparing a desired attitude of the human body with the current attitude; and transmitting an actuation signal to one or more of the tactile actuators based on the attitude deviation; wherein the tactile actuators are arranged to the carrier such that, when the carrier is used, the tactile actuators are (Continued)

arranged substantially in a reference plane; wherein the reference plane is functionally perpendicular to a central axis of a torso of the human body and the reference plane intersects the torso to define a circumference, wherein the tactile actuators are arranged to the circumference; and wherein the carrier comprises stretchable material such that the relative distance between the tactile actuators and/or between the tactile actuators and the sensor is maintained independent of the length of the circumference.

20 Claims, 4 Drawing Sheets

(51) Int. Cl.
  *A63B 26/00* (2006.01)
  *A63B 71/06* (2006.01)
(52) U.S. Cl.
  CPC .. *A63B 71/0619* (2013.01); *A63B 2071/0655* (2013.01); *A63B 2220/18* (2013.01); *A63B 2220/40* (2013.01); *A63B 2220/51* (2013.01); *A63B 2220/803* (2013.01)

(58) Field of Classification Search
  CPC ............ A63B 2220/18; A63B 2220/40; A63B 2220/51; A63B 2220/803; A63B 2209/10; A61B 5/4023; A61B 2560/0209; A61B 5/1116; A61B 5/6831; A61B 5/7455; A61B 5/1117
  See application file for complete search history.

(56) References Cited

OTHER PUBLICATIONS

International Search Report and Written Opinion; PCT Patent Application No. PCT/NL2020/050489; dated Sep. 28, 2020; 12 pages.
Kingma et al., "Vibrotactile Feedback Improves Balance and Mobility in Patients with Severe Bilateral Vestibular Loss", J Neurol, vol. 266, No. 1, 2019, pp. 19-26.

\* cited by examiner

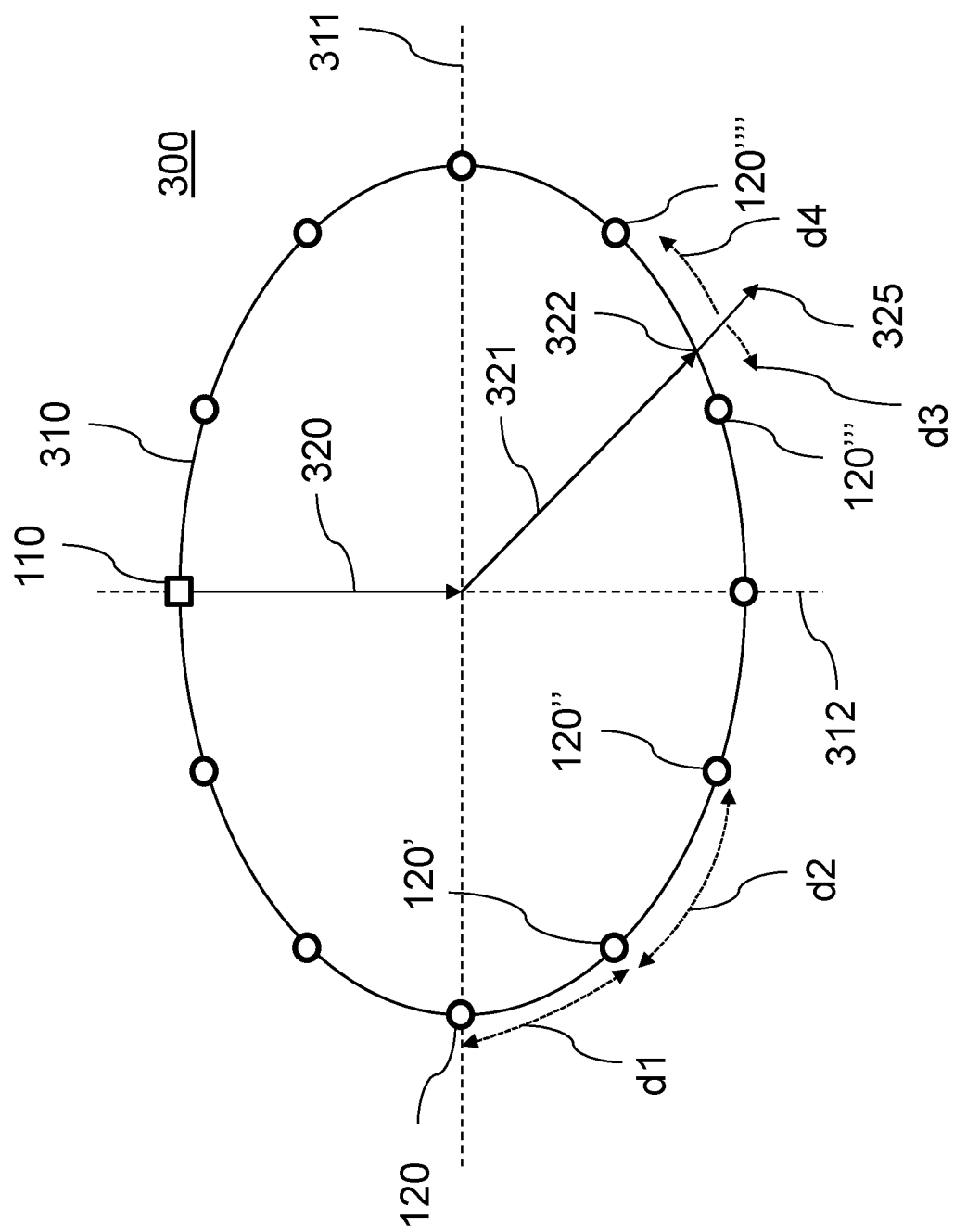

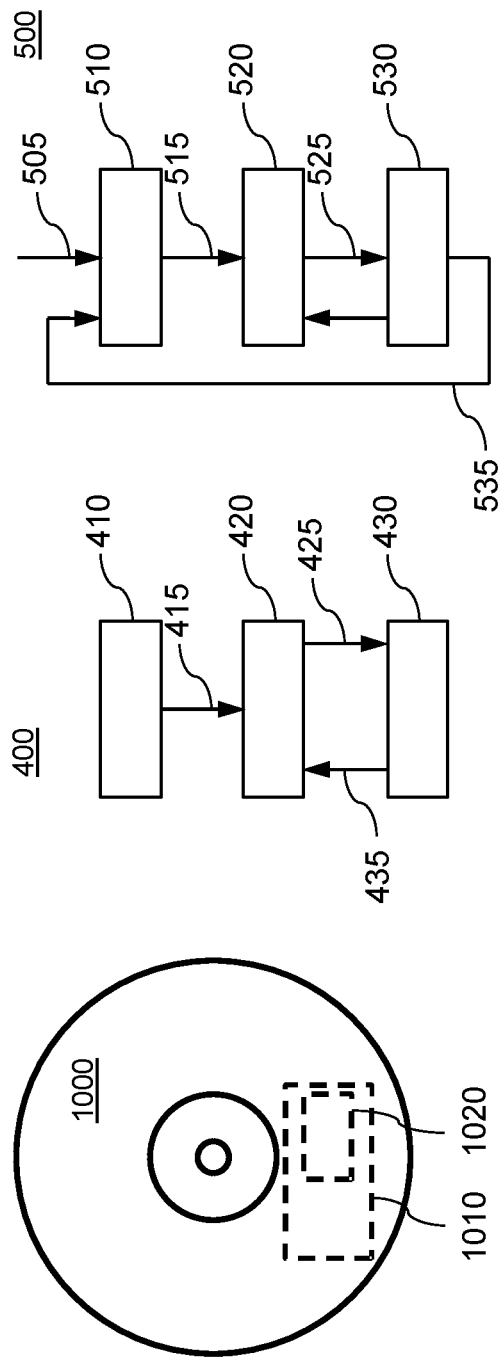

VIBROTACTILE FEEDBACK ARRANGEMENT

RELATED APPLICATIONS

This application is a U.S. National Phase of PCT Patent Application No. PCT/NL2020/050489 having International filing date of Jul. 7, 2020, which claims the benefit of priority of Dutch Patent Application No. 2023588 filed on Jul. 29, 2019. The entire contents of the above-referenced applications and of all priority documents referenced in the Application Data Sheet filed herewith are hereby incorporated by reference for all purposes.

FIELD OF THE INVENTION

The invention relates to the field of vibrotactile feedback arrangements.

BACKGROUND OF THE INVENTION

Bilateral vestibular loss is a chronic condition of which the causes can be ototoxic, infectious, traumatic, autoimmune or congenital. Also, in a substantial amount of cases no cause can be found. Patients suffering from bilateral vestibular loss may feel unstable and may even fall occasionally without reason causing injuries to themselves.

In recent years a balance belt has been developed to aid people suffering from bilateral vestibular loss to maintain their stability. The balance belt is basically a heavy belt worn by a patient around the waist. The belt contains a sensor sensing the upright position of the patient and several tactile actuators positioned in the belt. Such a belt is used in a study described in the article titled "Vibrotactile feedback improves balance and mobility in patients with severe bilateral vestibular loss" published on 5 Dec. 2018 in the Journal of Neurology.

Further, in WO 2009/029834 a motional training is achieved by providing a subject with vibrotactile feedback in response to an attempt by the subject to perform predetermined motions. In particular, an attempt by the subject to perform at least one predetermined motion is monitored using sensors, such as force plates or inertial sensors. The sensor signals indicate results of the attempt by the subject to perform the at least one predetermined motion, and a variance between the at least one predetermined motion and the results of the attempt by the subject to perform the at least one predetermined motion is determined. Vibrotactile signals are then sent to the subject by activating one or more actuators coupled to the subject, where the one or more actuators are spatially oriented with respect to the subject to indicate one or more directions. The vibrotactile signals indicate the variance with respect to the one or more directions.

A disadvantage of the known balance belt is that the production is complex. A further disadvantage of the known belt is that the belts are custom made obstructing introduction of the belt to the greater public. A further disadvantage is that the known belt is causing discomfort among others due to its bulkiness and heaviness.

SUMMARY OF THE INVENTION

An object of the invention is to improve the effectiveness of a vibrotactile feedback arrangement. Another object of the invention is to improve and/or simplify production of the vibrotactile feedback arrangement for allowing introduction to the greater public.

According to a first aspect of the invention, a vibrotactile feedback arrangement for use arranged to a human body, comprising:
a sensor arranged for sensing a current attitude of the human body relative to the environment;
tactile actuators arranged for allowing the human body to perceive an attitude deviation;
an elongated carrier for holding the tactile actuators and the sensor in tactile communication with the human body and for holding the tactile actuators and the sensor substantially fixed relative to the human body; and
a processing unit configured for:
receiving the current attitude from the sensor;
determining the attitude deviation based on comparing a desired attitude of the human body with the current attitude; and
transmitting an actuation signal to one or more of the tactile actuators based on the attitude deviation;
wherein the tactile actuators are arranged to the carrier such that, when the carrier is in use, the tactile actuators are arranged substantially in a reference plane;
wherein the reference plane is functionally perpendicular to a central axis of a torso of the human body and the reference plane intersects the torso to define a circumference, wherein the tactile actuators are arranged to the circumference; and
wherein the carrier comprises stretchable material having a stretch in a range of 5% to 25%, and stretchable substantially along the whole circumference, such that the relative distance between the tactile actuators and/or between the tactile actuators and the sensor is maintained independent of the length of the circumference.

The vibrotactile feedback arrangement is used to provide a wearer or user of the arrangement to perceive feedback in the form of a sense of touch. As tactile feedback is sensed typically with the skin, the arrangement is in use in communication, such as in contact, with the skin of the human body. Typically, the arrangement is arranged to or positioned around the torso of the human body, such as in contact with the torso.

The sensor is arranged for sensing a current attitude of the human body relative to the environment. The sensor is typically in contact with the human body or torso, such that the attitude of the human body or torso is sensed. The sensor may be a tilt sensor or inclinometer using gravity and/or the earth's magnetic field. Alternatively, the sensor may be a location sensor, such as a GPS sensor, or an orientation sensor, such as an earth magnetic field sensor.

The tactile actuators are arranged for allowing the human body to perceive the attitude deviation. The tactile actuators are preferably in contact with the human body or torso to convey the tactile information to the human body or torso. The tactile actuators may convey the tactile information to the human body or torso through mechanical means, such as vibrating parts. Alternatively, the information may be conveyed with the use of electricity. Other haptic or tactile actuators are within the scope of the invention.

The elongated carrier functionally holds the tactile actuators and the sensor in tactile communication with the human body and is substantially fixed relative to the human body. The elongated carrier may hold, fixate or couple the tactile actuators and the sensor to the carrier. Furthermore, the elongated carrier holds, fixates or couples the tactile actuators with the human body or torso for tactile communication.

The tactile actuators and the sensor may be more effective if the tactile actuators and the sensor are held substantially fixed to the human body or torso. Shifting of tactile actuators and the sensor typically cause inaccuracy of the vibrotactile feedback arrangement and should therefore be prevented as much as possible. The elongated carrier may also be typed as an elongated frame or an elongated holder.

The processing unit operationally couples the sensor to the tactile actuators. The processing unit may be a processor executing software. The processing unit may comprise several processors executing software, wherein the processors are distributed over the vibrotactile feedback arrangement. Alternatively, the processing unit may comprise electronics for executing the steps.

The processing unit is configured for or is configured for the steps of:
- receiving the current attitude from the sensor;
- determining the attitude deviation based on comparing a desired attitude of the human body with the current attitude; and
- transmitting an actuation signal to one or more of the tactile actuators based on the attitude deviation.

The desired attitude is typically set during a calibration sequence. Alternatively, the desired attitude may be set, such as introduced in the vibrotactile feedback arrangement through an additional interface. The additional interface might be a wired or wireless connection. The additional interface might be an interface comprising buttons and, a display, a LED and/or haptic feedback.

The tactile actuators may provide some type of direction or attitude indication. If the tactile actuators are arranged in or substantially in a reference plane and the tactile sensors are arranged to the human body for tactile communication in use, the reference plan intersect with the human body or torso. The reference plane intersecting with the human body or torso defines a circumference. The tactile actuators arranged along or substantially along this circumference advantageously allows the tactile actuators to provide an improved or more accurate direction or attitude to the user.

The human body or torso has a central axis, medial axis, craniocaudal axis or longitudinal axis. To further specify the location of the reference plane, the claim positions or locates the reference plane perpendicular or cross to the central axis. Thus, the circumference is typically a circumference of the torso. Even more specifically, the reference plane is preferably located at the height of the waist of the torso. In this case the carrier may advantageously be in the shape of a belt.

Every human is different, hence every human body is different. Even twins develop differently. The circumference as defined above will therefore have a different length. It is an insight of the inventor that to adopt to this variation in length a carrier may be made of stretchable material, such that one or a limited number of carriers can be produced to fit all circumferential lengths. And it is a further insight of the inventor that the carrier needs to comprise stretchable material in such a way, that the relative distance between the tactile actuators and/or between the tactile actuators and the sensor is maintained independent of the length of the circumference. If the relative distribution along the circumference is advantageously maintained, no additional calibration of the position of the tactile sensors is required while still providing a highly accurate actuation signal. Hence, the current invention provides the advantage of a simplified calibration and/or a simplified production.

In an embodiment, the carrier may be in whole or substantially in whole made of stretchable material. In this embodiment, the carrier typically comprises one type of stretchable material for maintaining the relative distances. The carrier is typically stretchable along the whole length of the circumference for maintaining the relative distances. Stretchable material is typically also flexible. Stretchable material is typically two-way stretchable, wherein the stretchable direction is at least along the elongated axis of the elongated carrier allowing the carrier to be adapted to the circumference length. The stretch of the stretchable material is typically in the range of 5% to 25% stretch, more specific 5% to 20%, even more specific 5% to 15%, even more specific substantially around 10%, preferably substantially 10%. In another embodiment, the stretchable material may be four-way stretchable. In another embodiment, the stretch of the stretchable material is at least 5%, preferably 7%, more preferably 8%, even more preferably 9%, most preferably 10%. In another embodiment, the stretch of the stretchable material is at most 30%, preferably 25%, more preferably 20%, even more preferably 15%, most preferably 10%. In another embodiment, the stretch of the stretchable material is a combination of the preceding minimum and maximum limits of stretch. A higher range for the stretch allows the carrier to adapt to more different circumferences. This adoption to more different circumferences allows for a lower number of carriers of different and well selected lengths to be adaptable to the whole or substantially the whole range of circumferences of users. As the number of carriers may be limited by applying a relative high stretch, the production is simplified. Such a relative high stretch may range from 8% to 25% stretch, more specific 9% to 25%, even more specific 10% to 25%, even more specific substantially above 10%, preferably substantially 15%.

As an example of the stretch and circumference lengths, the table below shows different lengths that may be used for the different elongated carriers.

| Lengths | Relaxed (cm) | Stretched (cm) | Stretch (%) |
| --- | --- | --- | --- |
| 1 | 57 | 68 | 19 |
| 2 | 68 | 80 | 18 |
| 3 | 80 | 95 | 19 |
| 4 | 92 | 109 | 18 |
| 5 | 109 | 130 | 19 |

The stretch ratio or extension ratio is a measure of the extensional or normal strain of a stretchable material. If no pulling force is exerted on the stretchable material, the stretchable material is in the undeformed configuration. If a maximum pulling force is exerted on the stretchable material, the stretchable material gets into a permanently deformed configuration. The maximum pulling force may be defined as the pulling force just not breaking or permanently deforming the stretchable material. An alternative definition of the maximum pulling force may be defined as the maximum pulling force still allowing breathing and/or comfortable wearing. The alternative maximum pulling force may be considerably lower than the previous maximum pulling force. The advantage of keeping the pulling force lower than the alternative maximum pulling force has the advantage that stretched material typically has an extended lifetime, such as more durable, or even imperishable. A ratio is defined by dividing the deformed configuration by the undeformed configuration. The stretch of a material may be defined as subtracting 100% from this ratio.

In an embodiment of the invention, the tactile actuators are substantially evenly distributed over the circumference. The even distribution of or interval between the tactile actuators allows for the tactile actuators to indicate the attitude deviation over the length of the circumference to be communicated to the human body or torso with the same accuracy over this complete length of the circumference. Furthermore, due to this even distribution, the relative distance between the tactile actuators is maintained with more ease as the elongated carrier is preferably in whole or substantially in whole of stretchable material, such as the same stretchable material.

In an embodiment of the invention, the tactile actuators and the sensor are substantially evenly distributed over the circumference. This even distribution allows a minimization of the influence of the tactile actuators on the measurement of the sensor, while the tactile actuators are still distributed well enough for allowing the tactile actuators to communicate the attitude deviation with enough accuracy. Furthermore, due to this even distribution, the relative distance between the tactile actuators and the sensor is maintained with more ease as the elongated carrier is preferably in whole or substantially in whole of stretchable material.

In an embodiment of the invention, the processing unit is configured for:
- associating the attitude deviation with a point on the circumference;
- selecting a first tactile actuator from the tactile actuators circumferencely nearest to the point on the circumference; and
- transmitting an actuation signal to the first tactile actuator. The attitude deviation may be represented by a vector having a direction, length and origin. The origin may be the central axis. The length of the vector may be the magnitude of the difference between the desired attitude and the current attitude. And the direction of the attitude deviation may be the direction of the subtraction of the desired attitude represented as a vector having a direction and the current attitude vector represented as a vector having a direction. Depending on the selected model, the central axis may be intersecting the circumference or the central axis may cross the centre point of the circumference.

In a further embodiment of the invention, the processing unit is configured for:
- selecting a second tactile actuator from the tactile actuators starting from the point along the circumference in the angular direction opposite to the first tactile actuator; and
- transmitting an actuation signal to the second tactile actuator. Typically, the attitude deviation is associated with a point on the circumference not coinciding with the location on the circumference of the tactile actuator. In this case, the associated point or virtual point is located between two tactile actuators, which are then selected for actuation. The associating of two tactile actuators may be seen as interpolating between the two locations of the tactile actuators located on the circumference.

In a further embodiment of the invention, the processing unit is configured for:
- calculating the actuation signal for the first tactile actuator and the second selected tactile actuator based on the distance of the respective selected actuators to the associated point or virtual point on the circumference. The closeness of the associated point or virtual point to the respective two tactile actuators may determine the amplitude or intensity of the actuation of the respective two tactile actuators. Typically, the square of the perceived amplitude of the tactile actuator equals the addition of the squared amplitudes of the two activated tactile actuators or in other words, the perceived energy of the tactile actuator equals the addition of the energies of the two activated tactile actuators. More specific, typically, the square of the perceived amplitude equals the addition of the squared amplitudes of the two activated tactile actuators. Even more specific, typically, a 1D Barycentric coordinate system may be applied taking into account the square or quadratic relationship for the energy or amplitude of the tactile actuators. As an example, the actuation may be inverse proportional to the distance between the tactile actuator and the associated point. In formula:

$$\beta = (p_v - p_1)/(p_2 - p_1)$$
$$p_1 = \text{point wherefor } \alpha = 1$$
$$p_2 = \text{point wherefor } \beta = 1$$
$$p_v = \text{virtual point between } p_1 \text{ and } p_2$$
$$\beta = \text{Barycentric coordinate of point } p_v$$
$$\beta A_1^2 \sim (1 - \beta) A_2^2$$
$$A_n = \text{actuation signal for actuator } n$$

In an embodiment of the invention, the processing unit is configured for:
- retrieving a circumference model of the circumference, which circumference model is a continuous curve with double line symmetry, wherein the symmetry lines are orthogonal and intersect at the origin of a polar coordinate system, wherein the origin is a point on the central axis and wherein the radius of the curve in the polar coordinate system is a continuous function;
- wherein said associating comprises:
- determining the point on the circumference model associated with the attitude deviation. It is an insight of the inventor that the tactile actuators need to be associated with locations in space. As a reference, the central axis is taken. The sensor may be located on the central axis, wherein the central axis is located close to the spine. Furthermore, the central axis may coincide with the circumference. Alternatively, the central axis may be located as centre point of the circumference, wherein the sensor may be located on the circumference and at a distance from the centre axis. Advantageously, a model is selected that easily allows scaling. A first order approximation of the waist of a human may be to select a circle as circumference. A second order approximation of the waist of a human may be to select an ellipse as circumference.

In an embodiment of the invention, the number of actuators is in the range of 4-20, preferably 6-16, more preferably 8-12, most preferably 10. Selecting a number of actuators inside the specified range provides the advantage of balancing the complexity of controlling multiple tactile actuators and on the other hand providing enough granularity that the direction of the attitude deviation may be communicated to the user of the arrangement. Increasing the number of tactile actuators increases the complexity of the control of all these actuators. The tactile actuators are typically daisy chained or placed in series. Tactile actuators are typically not stretchable, thus decreasing the number of tactile actuators improves the amount of stretch of the elongated carrier. Furthermore, tactile actuators are typically relative bulky and heavy compared to other parts of the vibrotactile feedback arrangement. A smaller number of tactile actuators would therefore cause improved wearing comfort during use. The granularity equals the distance between the tactile actuators measured along the circumference. This distance may not become too big that the direction of the attitude deviation cannot be communicated anymore with enough precision for the human using the arrangement to react correctly. It is a further insight that this granularity should also be selected such that the precision also suffices if the vibrotactile feedback arrangement is used by a human requiring the largest amount of stretch of the elongated carrier. Furthermore, in combination with the method of interpolation, this distance between actuators should be selected such that the activation of two tactile actuators is still perceived as a single virtual tactile actuator positioned between these two tactile actuators.

In an embodiment of the invention, the tactile actuators are vibrating actuators. In a further embodiment of the invention, the vibrating actuators are arranged to vibrate in a direction substantially perpendicular to the human body. It is an insight of the inventor, that the perception of vibration is best felt by the human using the arrangement, when the vibration, working sweep or deflection of the vibration is perpendicular or right on to the human body.

Furthermore, the vibration perpendicular to the human body causes noise waves to travel also through the vibrotactile feedback arrangement. The noise waves may generate noise outside the vibrotactile feedback arrangement causing an audible signal. The elongated carrier comprising stretchable material dampens or even prohibits the transmission of noise waves in the elongated carrier. Thus, the combination of the elongated carrier comprising stretchable material and the vibration perpendicular to the human body provides the advantage of reducing noise while optimizing vibration perception.

In an embodiment of the invention, the carrier comprises light and/or flexible materials, wherein preferably these materials couple the tactile actuators to the carrier. Preferably, the whole or substantially the whole of the carrier is made of light, stretchable and/or flexible materials. Light and/or flexible materials further reduce the transmission of noise waves in the carrier and thus further reduce the audible noise the arrangement makes while tactile actuators are actuated. Specifically, if the tactile actuators are coupled to the carrier by this material, the noise waves are mainly restricted to the tactile actuators itself. A typical light and/or flexible material may be a woven material or textile. This type of material may also be made stretchable.

In an embodiment of the invention, the carrier is advantageously shaped as a belt, a vest, a tactical vest, a skin tight garment, pants, an overall, a bandoleer, a leotard, corset, band, hat or a jammer.

In an embodiment of the invention, the intensity of the actuation signal to the one or more of the tactile actuators is based on the magnitude of the attitude deviation. In a further embodiment, the actuation signal increases in steps, such as for a particular magnitude the tactile actuators are active for only half the intensity and for a particular magnitude the tactile actuators are active for the full intensity. In another embodiment, the intensity of the actuation signal increases continuously, such as linear, depending on the magnitude of the attitude deviation. The intensity of the actuation signal may be that the selected tactile actuator is actuated with a specific amplitude, such as the amplitude of a vibration. The intensity of the actuation signal may be that the selected tactile actuator is actuated with a specific duty cycle, wherein the tactile actuator vibrates at a high frequency and this vibration is switched on and off with a certain specified duty cycle. The intensity of the actuation signal may be that the selected tactile actuator is actuated with a particular signal shape, such as wherein the tactile actuator vibrates at a high frequency and the envelope of the amplitude of the vibration changes with a triangle for small attitude deviations and with a square for larger attitude deviations. The intensity of the actuation signal may be that the selected tactile actuator is actuated with a particular signal frequency, such as wherein the tactile actuator vibrates at a low frequency for small attitude deviations and with a high frequency for larger attitude deviations.

It is an insight of the inventor that the haptic and/or tactile feedback may comprise changes in intensity; time, rhythm or duration; and/or frequency for conveying attitude deviation information or status information of the vibrotactile feedback arrangement. The status information may comprise a battery status, such as a low battery status conveyed to the user by a change in tactile feedback, such as a change in frequency of the feedback or operating with a specific duty cycle.

In an embodiment of the invention, the processing unit is configured for:
  comparing the attitude deviation with a predefined deviation threshold; and
  assigning an inactive value to the actuation signal if the attitude deviation is below a predefined deviation threshold and otherwise assigning an active value to the actuation signal. Thus, if the magnitude of the attitude deviation exceeds a deviation threshold, the actuation signal contains an activating signal for one or more of the tactile actuators. This advantageously allows for the tactile actuators only to be activated if the attitude deviation has a significant value or magnitude. Otherwise, as there will always be a small attitude deviation in some direction, always one or more of the tactile actuators will be active causing discomfort to the user of the arrangement and draining the battery as actuating the tactile actuator is energy costly. Hence, this embodiment provides the advantage of battery preservation as well as increased comfort to user. The introduction of the deviation threshold may be seen as introducing a dead zone.

In a further embodiment of the invention, the processing unit is configured such that the intensity of the actuation signal is continually increasing for an increasing attitude deviation. This embodiment is specifically advantageous if combined with the feature of the attitude deviation threshold. The increase may be linear, quadratic, exponential, logarithmic or any other continuously increasing function.

In an embodiment of the invention, the intensity of the actuation signal to the one or more of the tactile actuators is independent of the magnitude of the attitude deviation. This provides the advantage of simplifying the implementation of the arrangement, while the variation in intensity may not be perceptible by the human using the arrangement. This embodiment is specifically advantageous if combined with the feature of the attitude deviation threshold providing the combination of ease of implementation while preserving battery power.

In an embodiment of the invention, the processing unit is configured such that determining the magnitude of the attitude deviation is also based on the change and/or the speed of change of the difference between the desired attitude of the human body and the current attitude. If the sensor senses that the human body is travelling at a particular speed away from the desired attitude, this speed may be taken into account during the step of determining the attitude deviation, specifically the magnitude of the attitude deviation. If the sensor senses that the human body is accelerating with a particular acceleration away from the desired attitude, this acceleration may be taken into account during the step of determining the attitude deviation, specifically the magnitude of the attitude deviation.

In an embodiment of the invention, the attitude is an angular deviation relative to the perpendicular.

In a typical embodiment, the attitude is defined as the orientation, disposition, posture or position of the vibrotactile feedback arrangement, specifically the sensor, in space. The orientation or position in space can be defined as the deviation from the perpendicular expressed in a unit of angle, such as degrees or radials. The deviation may thus be a specific type of the attitude deviation. The perpendicular is defined as perpendicular to the horizontal ground or alternatively as a lead line having a direction under the influence of gravity. This deviation may be compared to the combination of the pitch and roll as used for describing the attitude of an airplane. This embodiment of the vibrotactile feedback arrangement is particularly useful for patients suffering from bilateral vestibular loss.

Depending on the configuration of the arrangement, the one or more tactile actuator in the direction of the deviation or opposite of the deviation may be activated for providing the deviation information to the user.

In an embodiment of the invention, the processing unit is configured for:
   stopping the transmitting of the actuation signal to one or more of the tactile actuators when the attitude deviation does not change for a predefined amount of time. If the attitude deviation does not change over a period of time, it may be concluded that the vibrotactile feedback arrangement is not used or even worse, the user has fallen. In these cases, continuously actuating the tactile actuators will drain the battery as well as in the latter case will cause discomfort to the fallen user. Stopping the transmission will therefore advantageously improve the battery lifetime as well as the comfort of the user.

In an embodiment of the invention, the vibrotactile feedback arrangement comprises:
   closing means arranged on the end of the elongated carrier;
   closing means seat arranged on the opposite end of the elongated carrier relative to closing means; and
   a closing means sensor arranged for sensing if the closing means are arranged in the closing means seat;
   wherein the processing unit is configured for:
   receiving the closing means seat information from the closing means sensor;
   stopping transmission of the actuation signal to one or more of the tactile actuators when the closing means seat information indicates the closing means are not seated in the closing means seat. The vibrotactile feedback arrangement is, when worn by a user, fitted with closing means and closing means seat, such as a belt buckle and a belt buckle seat, has the closing means seated in the closing means seat. The transmission of the actuation signal to the tactile actuators should be prohibited if the closing means seat information indicates that the closing means are not seated in the closing means seat, thereby advantageously preventing draining of the battery while the arrangement is not in use or in contact with the human body of the user.

According to another aspect of the invention, a computer program product comprising a computer readable medium having computer readable code embodied therein, the computer readable code being configured such that, on execution by a suitable computer or a suitable processor or a suitable processing unit, the computer the processor or the processing unit is caused to perform the steps of the method in an embodiment according to the invention:
   providing a first ratio signal;
   generating a comparison signal;
   generating the controlled signal;
   outputting an excitation signal; and
   outputting the controlled signal.

According to another aspect of the invention, a computer program product comprising a computer readable medium having computer readable code embodied therein, the computer readable code being configured such that, on execution by a suitable computer a suitable processor or a suitable processing unit, the computer the processor or the processing unit is caused to perform the method specified in an embodiment according to the invention According to another aspect of the invention, a method for use of a vibrotactile feedback arrangement according to any of the embodiments, comprising the steps of:
   providing the vibrotactile feedback arrangement to a user;
   arranging the vibrotactile feedback arrangement to the human body, such as the torso or the waist, of the user;
   calibrating the vibrotactile feedback arrangement; and
   after calibrating, feeding back the attitude deviation via the tactile actuators. This method allows the user to experience all the advantages of the vibrotactile feedback arrangement according to the invention.

In an embodiment of the method, the step of arranging comprises the step of:
   removing all clothes layers or all but one clothes layer around the waist; and
   after removing, positioning the vibrotactile feedback arrangement around the waist. The tactile communication with the human body may advantageously be improved by direct contact between the vibrotactile feedback arrangement and the skin of the human body circumnavigating any damping effect of clothes, garments or other materials a person may wear around his body or torso.

BRIEF DESCRIPTION OF THE DRAWINGS

The invention will be apparent from and elucidated further with reference to the embodiments described by way of example in the following description and with reference to the accompanying drawings, in which:
FIG. 3 schematically shows a model of the circumference;
FIG. 4 schematically shows a method for a vibrotactile feedback arrangement;
FIG. 5 an embodiment of a computer program product;
and
   FIG. 6 schematically shows a method for providing vibrotactile feedback to a human body.

The figures are purely diagrammatic and not drawn to scale. In the figures, elements which correspond to elements already described may have the same reference numerals.

LIST OF REFERENCE NUMERALS

| | |
|---|---|
| 10 | human body |
| 11 | torso |
| 12 | central axis, medial axis or longitudinal axis |
| 20 | reference plane |
| 21 | circumference |
| 25 | the perpendicular |
| 100 | vibrotactile feedback arrangement |
| 110 | sensor |
| 120, 120', 120", 120''', 120'''' | tactile actuators |
| 130 | carrier |
| 131 | stretchable material |
| 132 | belt buckle |
| 133 | receiving part belt buckle, belt buckle seat |
| 140 | processing unit |
| 141 | connecting wire |
| 142 | connecting wire loop |
| 300 | model of the circumference |
| 310 | ellipse |
| 311 | x-axis |
| 312 | y-axis |
| 320 | first translation |
| 321 | second translation |
| 322 | end point, virtual point or associated point |
| 325 | attitude deviation |
| d1 | first distance along the circumference |
| d2 | second distance along the circumference |
| d3 | third distance along the circumference |
| d4 | fourth distance along the circumference |
| 400 | method |
| 410 | initiating |
| 415 | initiating ready |
| 420 | calibrating |
| 425 | calibration ready |
| 430 | operating |
| 435 | non-use detected |
| 500 | method |
| 505 | start |
| 510 | receiving |
| 515 | received |
| 520 | determining |
| 525 | determined |
| 530 | transmitting |
| 535 | transmitted |
| 1000 | computer program product |
| 1010 | computer readable medium |
| 1020 | computer readable code |

DETAILED DESCRIPTION OF EXEMPLARY EMBODIMENTS

The following figures may detail different embodiments. Embodiments can be combined to reach an enhanced or improved technical effect. These combined embodiments may be mentioned explicitly throughout the text, may be hint upon in the text or may be implicit. Equal numbers for features in different figures may reference to the equal features.

Figure 1:
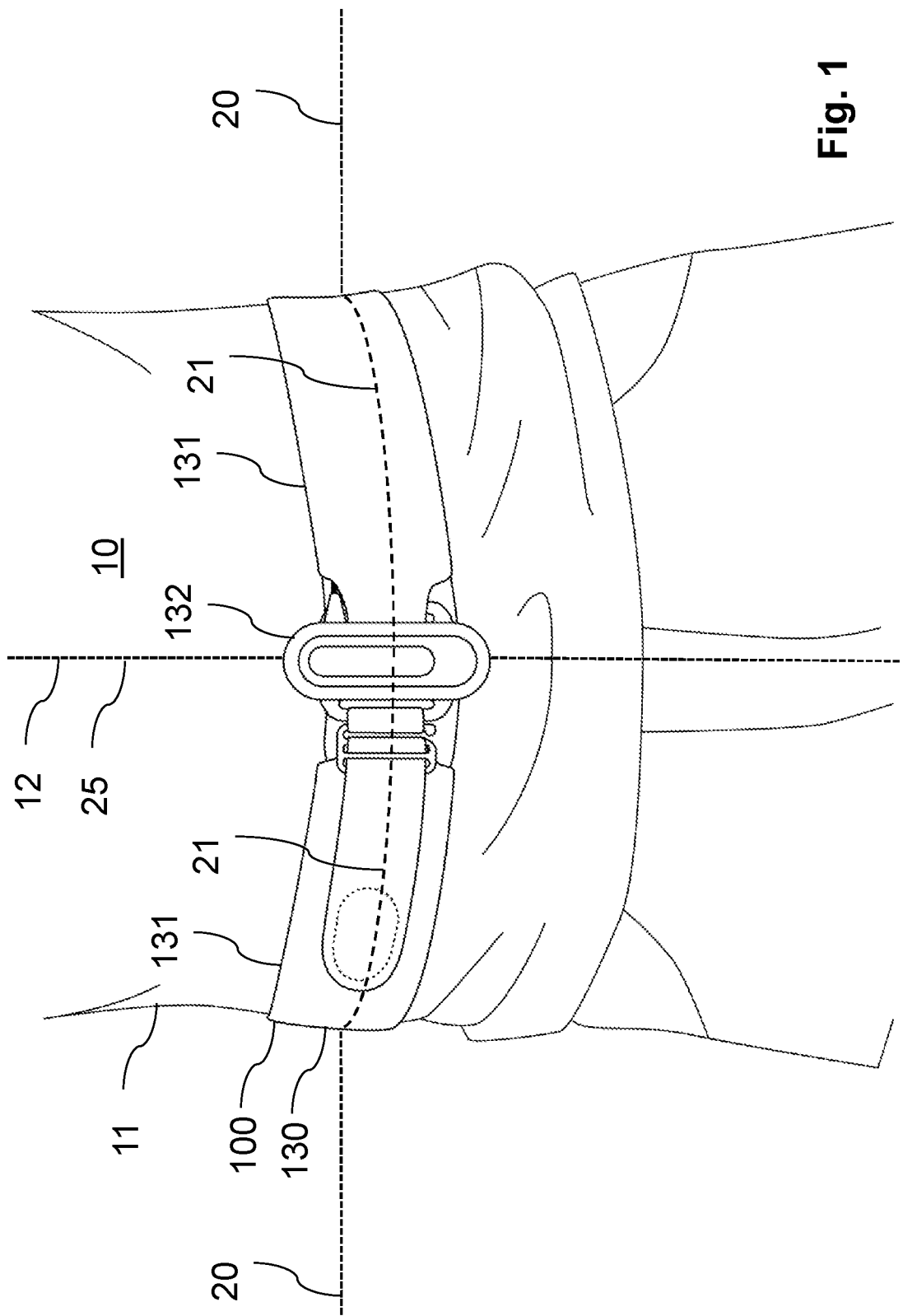
FIG. 1 schematically shows a vibrotactile feedback arrangement on a human body.

FIG. 1 schematically shows a vibrotactile feedback arrangement 100 on a human body 10 or more specific a torso 11. The vibrotactile feedback arrangement may be shaped as a belt. The torso has a central axis 12. The central axis, as the torso is upright, overlaps or coincides with a perpendicular 25. If the torso is placed under an angle, the central axis will be under this angle with the perpendicular. Furthermore, a reference plane 20 is shown. The reference plane is perpendicular or cross to the central axis.

Figure 2:
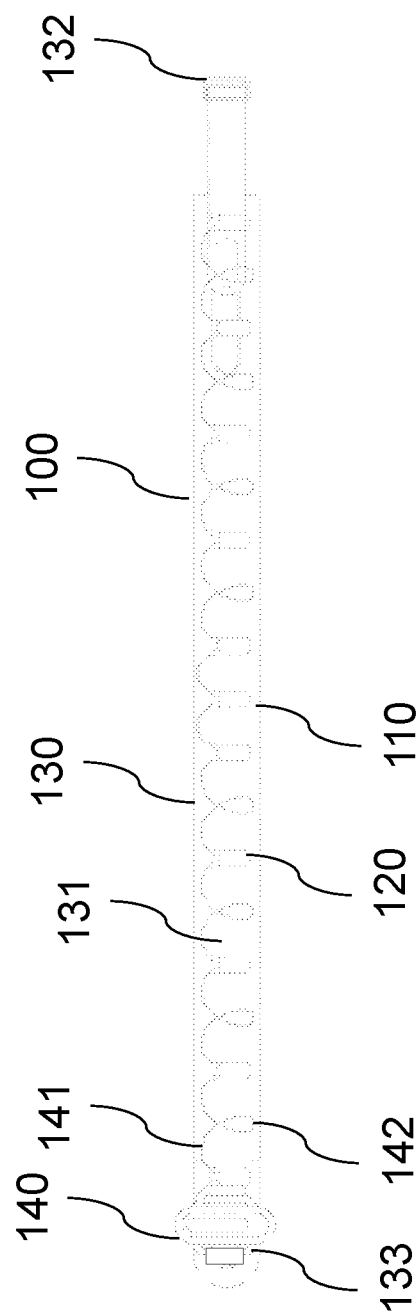
FIG. 2 schematically shows a vibrotactile feedback arrangement laid out.

The vibrotactile feedback arrangement comprises an elongated carrier 130, a sensor 110 (shown in FIG. 2) and tactile actuators 120, 120' (shown in FIG. 2). The sensor and tactile actuators are typically arranged on the inside of the carrier, such that the sensor and tactile actuators are both optimally in contact with the human body.

The vibrotactile feedback arrangement may comprise closing means, such as a belt buckle 132, and closing means seat, such as a belt buckle seat 133 (shown in FIG. 2).

The carrier arranges the tactile actuators and the sensor to the human body, in this case a torso, more specific to the waist of a torso. The tactile actuators and the sensor are in tactile communication with the human body and substantially fixed relative to the human body by the elongated carrier. For the sensor, this tactile communication allows the sensor to sense the change in the angle of the central axis relative to the perpendicular in all directions. Furthermore, for the sensor, the substantial fixation prevents the introduction of measurement errors by the sensor due to a shift of the sensor over the human body during use. For the tactile actuators, this tactile communication allows the tactile actuators to provide a tactile signal to the human body. Furthermore, for the tactile actuators, the substantial fixation prevents the introduction of inaccuracy of the position where the tactile signal is applied or provided to the human body.

The closing means may comprise also interfacing means for interfacing and/or operating the arrangement. The interfacing means may comprise one or more buttons, a display, and/or one or more LEDs. The interfacing means typically allow the arrangement to be controlled or set in a mode, such as operational mode, off mode, calibration mode. Alternatively, the arrangement may comprise a temperature sensor, hearth rate sensor or any other sensor for sensing if the arrangement is in contact with a human body for switching on and off, preferably in combination with the interfacing means having in use an overruling switch and/or timeout timer detecting inactivity of the human body on a tactile signal provided.

The reference plane 20 is arranged such that the plane intersects the carrier or belt substantially in the middle. The reference plane intersects the torso 11 to define a circumference 21. The tactile actuators and the sensor are preferably arranged to this circumference thereby providing the advantage of a tactile directional sense to the user.

The sensor may sense the change in angle of the central axis relative to the perpendicular. The sensing is typically in all direction of angular deviation from the central axis. Based on the sensing of the current attitude and the comparison with the desired attitude, tactile actuators may be actuated with an actuation signal. In an embodiment of the invention, one or more tactile actuators substantially in the direction of the deviation from the desired attitude may be activated. In another embodiment of the invention, one or more tactile actuators substantially opposite to the direction of the deviation from the desired attitude may be activated.

FIG. 2 schematically shows a vibrotactile feedback arrangement 100 laid out. The arrangement comprises an elongated carrier 130. The arrangement may further comprise a belt buckle 132 and a belt buckle seat 133 arranged on opposite sites of the elongated carrier. The carrier is flexible and can therefore be wrapped around a torso, such as a waist of the human body. When wrapped, the belt buckle and belt buckle seat are shaped to couple together to form a loop. The belt buckle and belt buckle seat or more generic the closing means and the closing means seat may be shaped according to multiple embodiments as long as it provides the functionality of coupling to form a loop together with the elongated carrier. As the elongated carrier is stretchable substantially along the whole circumference, the closing means are typically the part along the circumference being not stretchable. The length that the closing means stretch out along the circumference is advantageously kept as short as practically possible to assure the technical effect of the stretchable elongated carrier. In practice typically, the closing means together with the elongated carrier cover the circumference. The ratio between the length covered by elongated carrier and the length covered by the closing means is in the range of more than 90%, preferably 95%. Furthermore, to minimize the distorting effect of different circumference lengths, the closing means are typically worn on the front of the human body and the sensor is arranged to the spine. The arrangement typically comprises a processing unit 140. The processing unit may optionally be integrated with several other features. The processing unit may comprise interfacing means for interfacing, operating and/or setting the arrangement in a specific mode and/or adjusting a setting of the arrangement. The processing unit typically comprises a processor executing software. The software comprises commands for executing, at least in part, one of the methods mentioned throughout this text. Alternatively, the processing unit executes the method in programmable logic, such as an FPGA or dedicated logic, such as an ASIC.

The arrangement typically comprises one sensor 110. As the sensor is sensitive to changes in position due to shift or touch, the sensor is typically located at a location that is relatively insensitive to shift or touch, such as the back of the human body or torso, such as in contact with the spine. As the closing means and the closing means seat are preferably placed in front for easily closing the arrangement, the sensor is typically arranged half-way the elongated carrier. Furthermore, as another advantage, the processing unit, when comprising interfacing means, may be touched or pressed upon when in use, making it an even less favourable location for arranging the sensor close to the processing unit. Furthermore, the belly, especially the front part of the belly may move due to breathing, while the spine is relatively stable even when breathing heavily, making the spine a favourable location for positioning the sensor.

The other, similar shaped objects as the sensor may be tactile actuators 120, 120'. The tactile actuators and the sensor may be are arranged at equal distances in this embodiment. A preferred embodiment has the tactile actuators arranged at equal distances, wherein preferable the sensor is arranged between two tactile actuators and at the spine in use, wherein further preferable the number of tactile actuators equals ten. As the distance between the sensor and the nearest tactile actuators is maximized, the disturbance of the tactile actuators to the sensor measurement is minimized, while maintaining sufficient granularity of providing a directional sense to the human body or torso. The spine or the back is typically relatively insensitive to touch, providing a preferred location for locating the sensor. A disadvantage of location the sensor next to the spine may be when the user carries a backpack, which may be the case when using the vibrotactile feedback arrangement as a personal guidance system. Also, if the arrangement is around the waist and the sensor is located in contact with the spine, the spine provides a relative stable base. The vibrations from a first tactile actuator may travel further towards a second tactile actuator through hard tissue, such as bone. Furthermore, the vibrations from a first tactile actuator may travel a shorter distance towards a second tactile actuator through soft tissue, such as fat and/or thick skin, due to absorption of the vibrations. This hard tissue causes the vibrations from two proximate tactile actuators to overlap and generate a vibration sensation to the human body located between the respective proximate tactile actuators while the two respective proximate tactile actuators are relatively far apart. A disadvantage of tissue, specifically hard tissue, is that the vibrations may propagate in detrimental directions causing tactile or haptic perceptions in undesirable locations misguiding the user or causing a deviation in the perceived direction. Hence, the invention limits vibrations in tissue, such as hard tissue, as much as possible. Another influence on the distance between two respective proximate tactile actuators is the sensitivity of the skin to tactile and/or haptic stimulation. An important factor to this sensitivity is the amount of nerve endings in the skin. Tests have shown that the back or spine area is relatively insensitive and comprises typically relatively hard tissue, and the belly or front area is relatively sensitive and comprises typically relatively soft tissue. Following from these tests is that interpolation may be combined with less tactile actuators arranged to the back such that the user will still perceive the interpolating tactile actuators as one tactile actuator and not as two single tactile actuators. Further following from these tests is that interpolation may be combined with more tactile actuators arranged to the front such that the user will still perceive the interpolating tactile actuators as one tactile actuator and not as two single tactile actuators. Hence, in a preferred embodiment, the vibrotactile feedback arrangement comprises an uneven distribution of the tactile actuators for minimizing the number of tactile actuators, while being able to apply interpolation between tactile actuators over the whole circumference. In a further preferred embodiment, the uneven distribution comprises eight tactile actuators and preferably has the sensor arranged at the back or spine. The minimization of the tactile actuators has the effect of improving the comfort of the user as the weight is reduced and the number of inflexible actuators is reduced.

The effect of vibrations travelling through the tissue of the user or through the vibrotactile feedback arrangement may cause crosstalk between tactile actuators or between a tactile actuator and the sensor. Depending on the situation, such as described above, crosstalk may be used, such as for interpolation or can be undesirable, such as between the tactile actuator and the sensor or at locations with specifically hard tissue.

The elongated carrier is next to flexible also made of stretchable material 131. This allows for the arrangement to be used by user having different sizes in body. This obviates the need for costly, timely adjustments to the length of the elongated carrier, thereby increasing complexity of the production process of the arrangement. Furthermore, if adjustment means are present in the prior art, the prior art belt requires adjustment to each user during first use. Also, during use, the prior art belt may require adjustment due to the change in size of the user. Or even worse the user does not adjust when his body changes size and the prior art belt will start performing inferior or fail altogether. The arrangement according to the invention allows the carrier to adjust to the size of the user each time the arrangement is placed around the human body or torso.

The elongated carrier comprises stretchable material, such that the relative distance between the tactile actuators and/or between the tactile actuators and the sensor is maintained independent of the length of the circumference. Further, the elongated carrier is preferably substantially made from stretchable material. As the stretchable material, when stretched to some random length, causes the tactile actuators and/or the tactile actuators and the sensor to not or substantially not move relatively to each other, this simplifies the actuation or calculation for the actuation of the tactile actuators.

The elongated carrier holding the tactile actuators and the sensor may further comprise a connecting wire 141. The connecting wire connects the tactile actuators, sensor and processing unit for allowing communication and preferably also distributing electrical power between them. Typically, the connecting wire comprises segments connecting one element with the other forming a series circuitry or daisy chain. As the carrier is stretchable, the segment of the connecting wire makes a loop 142 between the elements to allow for this stretch. In an alternative embodiment, the connecting wire is made of stretchable electrically conductive material. This allows for smaller loops or even omitting the loops. In combination with arranging the connection points at opposite sides of the tactile actuators and arranging the elongated tactile actuators to the elongated carrier, this allows for the elongated carrier to be made smaller.

FIG. 3 schematically shows a model 300 of the circumference, which may be modelled as a circle or ellipse 310. The ellipse has a centre point, which is selected as the origin of the Euclidian space having an x-axis 311 and a y-axis 312. The x-axis coincides with the centre point of the ellipse and the two points of the ellipse furthest away from the centre point. The y-axis coincides with the centre point of the ellipse and the two points of the ellipse closest by the centre point.

The sensor 110 may be arranged to the spine and thus the back of the human body. The sensor is typically arranged on a location where the y-axis coincides with the y-axis. The closing means and the closing means seat are typically arranged on the opposite side of the circumference, which may be substantially the middle of the belly.

The sensor and the tactile actuators 120, 120', 120", 120''', 120'''' are typically arranged at equal or substantially equal distances along the circumference or ellipse. The distance d1 between a first tactile actuators 120 and a second tactile actuator 120' is shown by a first dotted arrow. The distance d2 between a second tactile actuators 120' and a third tactile actuator 120" is shown by a second dotted arrow. The elongated carrier has a length substantially equal to the length of the circumference. Furthermore, the elongated carrier comprises stretchable material to adapt to the length of the circumference. Thus, depending on the human body or torso, the ellipse may be scaled, such as blown-up or shrunk. As the tactile actuators and the sensor are held by the carrier, the tactile actuators and the sensor may shift or have a change in distance relative to the centre point, but the angle of each tactile actuator and sensor relative to the centre point, x-axis and y-axis is maintained. In other words, the relative distance, which may be defined as d1/d2, is constant or maintained if the length of the circumference changes. Maintaining the relative distance between tactile actuators and/or tactile actuators and the sensor may be defined as a first distance between a first and a second tactile actuator and a second distance between the second and a third tactile actuator, wherein the first distance divided by the second distance is constant and/or a first distance between a sensor and a first tactile actuator and a second distance between the sensor and a second tactile actuator, wherein the first distance divided by the second distance is constant, respectively.

During operation, the sensor may measure a current attitude. The current attitude is first compared to a desired attitude resulting in an attitude deviation. The comparison may be a subtraction of the current attitude from the desired attitude. The attitude deviation is typically a direction and optionally a strength or intensity. The attitude deviation is placed at the centre point of the ellipse with a first translation 320. The attitude deviation is placed from the centre point on a point on the ellipse with a second translation 321. The second translation follows the direction away from the centre point and coincides with the ellipse defining an end point 322 or associated point of the translation. The translated attitude deviation 325 is shown at the end point. The translated attitude deviation has typically a direction and optionally a strength or intensity equal to the attitude deviation before translation.

The end point has a third distance d3 along the circumference to a fourth tactile actuator 120'''. The end point further has a fourth distance d4 along the circumference to a fifth tactile actuator 120''''. In this example, the third distance d3 is smaller compared to the fourth distance d4. In an embodiment, the processing unit may then actuate the fourth tactile sensor only. Typically, the actuation of the tactile actuator is not dependent on the strength of the attitude deviation. The actuation may comprise the implementation of a dead zone. Alternatively, the actuation of the tactile actuator is dependent on the strength of the attitude deviation. The actuation may comprise the implementation of a dead zone. The direction indicated by the distance d3 from the end point to the fourth tactile actuator may be typed as a first angular direction along the circumference. The direction indicated by the distance d4 from the end point to the fifth tactile actuator may be typed as a second angular direction along the circumference. The second angular direction is opposite to the first angular direction.

In another embodiment, the processing unit may then actuate the fourth and fifth tactile actuator. This may be labelled interpolation. Typically, the actuation of the two tactile actuators is not dependent on the strength of the attitude deviation. The actuation may comprise the implementation of a dead zone. Alternatively, the actuation of the tactile actuators is dependent on the strength of the attitude deviation. The intensity of the actuation of the fourth and fifth actuators may be dependent on respectively the fourth distance and the third distance, thus in reverse order. The average intensity may then be maintained and the intensity can be distributed over the two actuators, such that the actuator closest to the end point, the fourth actuator in this case, is actuated with a higher intensity compared to the fifth actuator. Actuating multiple actuators in this way allows the system to provide to the human body a direction perception with a much higher granularity compared to the number of actuators. The actuation may comprise the implementation of a dead zone.

The advantage of using stretchable material according to the invention, allows for this model to scale, without changing the calculation for the processing unit, thus the processing is simplified. Specifically, this advantage may be reached with a model allowing scaling as described above. Typical models are symmetric around the x-axis and y-axis.

FIG. 4 schematically shows a method 400 for a vibrotactile feedback arrangement 100. The method may be partly or completely implemented in the processing unit. The method starts with the step of initiating 410. During initiating the arrangement, specifically the processing unit, starts up and is set in a mode ready for calibration.

As soon as the initiating step is completed, the method transfers 415 to the step of calibrating 420. The calibrating step may comprise setting the desired attitude. The desired attitude may be set by standing up straight for a predefined amount of time. The desired attitude may be set by receiving this attitude from an external source, such as an input device or communication device. The desired attitude may be a geographical location. After the calibration step is completed, the arrangement may provide a tactile or visual indication to the human body or eye of the human body, respectively, providing a feedback of completion of the calibration.

The calibration step may comprise a verification step. The verification step may comprise enabling each individual tactile actuator, such as sequentially actuating, for verifying that the vibration of the tactile actuator is perceivable by the human body. Sequentially actuating the tactile actuators for a predefined amount of time provides the advantage that if one of the tactile actuators is failing to function or vibrate, this gap in vibration will be noticed by the human body.

After the calibrating step is completed, the method transfers 425 to the step of operation 430. In operation the arrangement provides the feedback as described and claimed when the current attitude deviates from the desired attitude.

If the arrangement detects that the arrangement is not any more in contact with the human body or the attitude deviation is not reduced for a predefined amount of time then the arrangement may transfer 435 to the calibrating step. Alternatively, arrangement may transfer to a sleep mode or low-power mode. And if activity is detected the arrangement may transfer to the calibration mode for first calibrating before being operational.

The user may also transfer 435 the arrangement from operation 430 to the calibrating 420, when present, by a short push on a button. The user may also switch off the arrangement, when present and switched on, by a long pushing on the button, such as longer than 3 seconds. The user may also switch on the arrangement, when present and switched off, by a long pushing on the button, such as longer than 3 seconds.

FIG. 5 schematically shows an embodiment of a computer program product, a computer readable medium and/or a non-transitory computer readable storage medium 1000 having a writable part 1010 including a computer program 1020, the computer program including instructions for causing a processor system to perform a method according to the invention.

FIG. 6 schematically shows a method 500 for providing vibrotactile feedback to a human body. The method starts 505 with receiving 510 a current attitude of the human body relative to the environment from a sensor arranged for sensing a current attitude of the human body relative to the environment. When the attitude is received 515, the method continues with determining 520 the attitude deviation based on comparing a desired attitude, which may be the calibration value determined when the calibration is ready 425, of the human body with the current attitude. When the attitude deviation is determined 525, the method continues with transmitting 530 an actuation signal to one or more tactile actuators of tactile actuators based on the attitude deviation. The method typically loops back to the step of receiving after completing the transmitting step. The loopback may be delayed in time to save battery power. The delay may be adaptive such that battery power is preserved when the human body is in relative rest, and the feedback rate and/or accuracy is increased when the human body is moving or having an attitude deviation typically beyond a threshold.

It should be noted that the figures are purely diagrammatic and not drawn to scale. In the figures, elements which correspond to elements already described may have the same reference numerals.

It will be appreciated that the invention also applies to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing stage of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a data storage, such as a ROM, for example, a CD ROM or a semiconductor ROM, flash memory or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

The term "substantially" herein, such as in "substantially all emission" or in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of".

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or stages other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage. Substantially is to be understood as a range around the stated feature. This range may be defined as comprising the production variation provided by the current most common production techniques. Functionally is to be understood as relating two features to each other in such a way that these features are able to perform a specific function.

Examples, embodiments or optional features, whether indicated as non-limiting or not, are not to be understood as limiting the invention as claimed.

The invention claimed is:

1. A vibrotactile feedback arrangement for use arranged to a human body, comprising:
   a sensor arranged for sensing a current attitude of the human body relative to the environment;
   tactile actuators arranged for allowing the human body to perceive an attitude deviation;
   an elongated carrier for holding the tactile actuators and the sensor in tactile communication with the human body and for holding the tactile actuators and the sensor substantially fixed relative to the human body; and
   a processing unit configured for:
   receiving the current attitude from the sensor;
   determining the attitude deviation based on comparing a desired attitude of the human body with the current attitude; and
   transmitting an actuation signal to the tactile actuators based on the attitude deviation;
   wherein the tactile actuators are arranged to the carrier such that, when the carrier is used, the tactile actuators are arranged substantially in a reference plane;
   wherein the reference plane is functionally perpendicular to a central axis of a torso of the human body and the reference plane intersects the torso to define a circumference, wherein the tactile actuators are arranged to the circumference; and
   wherein the carrier comprises stretchable material having a stretch in a range of 5% to 25%, and stretchable substantially along the whole circumference, such that the relative distance between the tactile actuators and between the tactile actuators and the sensor is maintained independent of the length of the circumference.

2. The vibrotactile feedback arrangement according to claim 1, wherein the stretchable material has a stretch in a range of 8% to 25%.

3. The vibrotactile feedback arrangement according to claim 1, wherein the tactile actuators are substantially evenly distributed over the circumference.

4. The vibrotactile feedback arrangement according to claim 1, wherein the processing unit is configured for:
   associating the attitude deviation with a point on the circumference;
   selecting a first tactile actuator from the tactile actuators circumferencely nearest to the point on the circumference; and
   transmitting an actuation signal to the first tactile actuator.

5. The vibrotactile feedback arrangement according to claim 4, wherein the processing unit is configured for:
   selecting a second tactile actuator from the tactile actuators starting from the point along the circumference in the angular direction opposite to the first tactile actuator; and
   transmitting an actuation signal to the second tactile actuator.

6. The vibrotactile feedback arrangement according to claim 5, wherein the processing unit is configured for:
   calculating the actuation signal for the first selected tactile actuator and the second selected tactile actuator based on the distance of the respective selected actuators to the associated point on the circumference.

7. The vibrotactile feedback arrangement according to the preceding claim 4, wherein the processing unit is configured for:
   retrieving a circumference model of the circumference, which circumference model is a continuous curve with double line symmetry, wherein the symmetry lines are orthogonal and intersect at the origin of a polar coordinate system, wherein the origin is a point on the central axis and wherein the radius of the curve in the polar coordinate system is a continuous function;
   wherein said associating comprises:
   determining the point on the circumference model associated with the attitude deviation.

8. The vibrotactile feedback arrangement according to claim 1, wherein the number of actuators is in the range of 6-16.

9. The vibrotactile feedback arrangement according to claim 1, wherein the tactile actuators are vibrating actuators; and
   wherein the vibrating actuators are arranged to vibrate in a direction substantially perpendicular to the human body.

10. The vibrotactile feedback arrangement according to claim 9, wherein the carrier comprises light and flexible material, wherein this material couples the tactile actuators to the carrier.

11. The vibrotactile feedback arrangement according to claim 1, wherein the carrier is a belt, a vest, a tactical vest, a skin tight garment, pants, an overall, a bandoleer, a leotard or a jammer.

12. The vibrotactile feedback arrangement according to claim 1, wherein the intensity of the actuation signal to the tactile actuators is based on the magnitude of the attitude deviation; and
   wherein the processing unit is configured such that the intensity of the actuation signal is continually increasing for an increasing attitude deviation.

13. The vibrotactile feedback arrangement according to claim 1, wherein the processing unit is configured for:
   comparing the attitude deviation with a predefined deviation threshold; and
   assigning an inactive value to the actuation signal if the attitude deviation is below a predefined deviation threshold and otherwise assigning an active value to the actuation signal.

14. The vibrotactile feedback arrangement according to claim 1, wherein the processing unit is configured such that determining the magnitude of the attitude deviation is also based on the change of the difference between the desired attitude of the human body and the current attitude.

15. The vibrotactile feedback arrangement according to claim 1, wherein the attitude is an angular deviation relative to the perpendicular.

16. The vibrotactile feedback arrangement according to claim 1, wherein the processing unit is configured for:

stopping the transmitting of the actuation signal to the tactile actuators when the attitude deviation does not change for a predefined amount of time.

17. A method for providing vibrotactile feedback to a human body, comprising:
receiving a current attitude of the human body relative to the environment from a sensor arranged for sensing a current attitude of the human body relative to the environment;
determining the attitude deviation based on comparing a desired attitude of the human body with the current attitude; and
transmitting an actuation signal to the tactile actuators of tactile actuators based on the attitude deviation;
wherein the tactile actuators are arranged to an elongated carrier for holding the tactile actuators and the sensor in tactile communication with the human body and for holding the tactile actuators and the sensor substantially fixed relative to the human body;
wherein the tactile actuators are arranged to the carrier such that, when the carrier is used, the tactile actuators are arranged substantially in a reference plane;
wherein the reference plane is functionally perpendicular to a central axis of a torso of the human body and the reference plane intersects the torso to define a circumference, wherein the tactile actuators are arranged to the circumference; and
wherein the carrier comprises stretchable material having a stretch in a range of 5% to 25%, and stretchable substantially along the whole circumference, such that the relative distance between the tactile actuators is maintained independent of the length of the circumference.

18. A computer program product comprising a computer readable medium having computer readable code embodied therein, the computer readable code being configured such that, on execution by a suitable processor; the processor is caused to perform the steps of the method for providing vibrotactile feedback to a human body, comprising:
receiving a current attitude of the human body relative to the environment from a sensor arranged for sensing a current attitude of the human body relative to the environment;
determining the attitude deviation based on comparing a desired attitude of the human body with the current attitude; and
transmitting an actuation signal to the tactile actuators of tactile actuators based on the attitude deviation;
wherein the tactile actuators are arranged to an elongated carrier for holding the tactile actuators and the sensor in tactile communication with the human body and for holding the tactile actuators and the sensor substantially fixed relative to the human body;
wherein the tactile actuators are arranged to the carrier such that, when the carrier is used, the tactile actuators are arranged substantially in a reference plane;
wherein the reference plane is functionally perpendicular to a central axis of a torso of the human body and the reference plane intersects the torso to define a circumference, wherein the tactile actuators are arranged to the circumference; and
wherein the carrier comprises stretchable material having a stretch in a range of 5% to 25%, and stretchable substantially along the whole circumference, such that the relative distance between the tactile actuators is maintained independent of the length of the circumference.

19. A method for use of a vibrotactile feedback arrangement for use arranged to a human body, comprising:
a sensor arranged for sensing a current attitude of the human body relative to the environment;
tactile actuators arranged for allowing the human body to perceive an attitude deviation:
an elongated carrier for holding the tactile actuators and the sensor in tactile communication with the human body and for holding the tactile actuators and the sensor substantially fixed relative to the human body; and
a processing unit configured for:
receiving the current attitude from the sensor;
determining the attitude deviation based on comparing a desired attitude of the human body with the current attitude; and
transmitting an actuation signal to the tactile actuators based on the attitude deviation;
wherein the tactile actuators are arranged to the carrier such that, when the carrier is used, the tactile actuators are arranged substantially in a reference plane;
wherein the reference plane is functionally perpendicular to a central axis of a torso of the human body and the reference plane intersects the torso to define a circumference, wherein the tactile actuators are arranged to the circumference; and
wherein the carrier comprises stretchable material having a stretch in a range of 5% to 25%, and stretchable substantially along the whole circumference, such that the relative distance between the tactile actuators and between the tactile actuators and the sensor is maintained independent of the length of the circumference;
the method comprising the steps of:
providing the vibrotactile feedback arrangement to a user;
arranging the vibrotactile feedback arrangement to the human body of the user;
calibrating the vibrotactile feedback arrangement; and
after calibrating, feeding back the attitude deviation via the tactile actuators.

20. The method according to claim 19, wherein the step of arranging comprises the step of:
removing all clothes layers around the waist; and
after removing, positioning the vibrotactile feedback arrangement around the waist.

* * * * *